United States Patent
Hopple et al.

(10) Patent No.: US 10,092,274 B2
(45) Date of Patent: Oct. 9, 2018

(54) SUB-PERFORMING TRANSDUCER ELEMENT DETECTION FOR MEDICAL ULTRASOUND

(71) Applicant: Siemens Medical Solutions USA, Inc., Malvern, PA (US)

(72) Inventors: Jerry D. Hopple, Seabeck, WA (US); Dalong Liu, Shoreview, MN (US); Stephen R. Barnes, Bellevue, WA (US); David A. Petersen, Fall City, WA (US); Colin Brock, Renton, WA (US); John C. Lazenby, Fall City, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 406 days.

(21) Appl. No.: 14/261,303

(22) Filed: Apr. 24, 2014

(65) Prior Publication Data

US 2015/0157299 A1 Jun. 11, 2015

Related U.S. Application Data

(60) Provisional application No. 61/913,182, filed on Dec. 6, 2013.

(51) Int. Cl.
| | |
|---|---|
| *A61B 8/00* | (2006.01) |
| *A61N 7/00* | (2006.01) |
| *B06B 1/02* | (2006.01) |
| *G01S 7/52* | (2006.01) |
| *G01S 15/89* | (2006.01) |
| *A61B 17/00* | (2006.01) |

(52) U.S. Cl.
CPC .............. *A61B 8/58* (2013.01); *A61B 8/4483* (2013.01); *B06B 1/0207* (2013.01); *G01S 7/5205* (2013.01); *G01S 15/8915* (2013.01); *A61B 2017/00725* (2013.01); *A61N 7/00* (2013.01); *A61N 2007/0078* (2013.01); *B06B 2201/20* (2013.01); *B06B 2201/51* (2013.01); *B06B 2201/55* (2013.01); *B06B 2201/76* (2013.01)

(58) Field of Classification Search
CPC ........ A61B 2017/00725; A61B 8/4483; A61B 8/58; A61N 2007/0078; A61N 7/00; B06B 1/0207; B06B 2201/20; B06B 1/51; B06B 1/55; B06B 1/76; G01S 15/8915; G01S 7/5205
See application file for complete search history.

(56) References Cited

U.S. PATENT DOCUMENTS

| | | | | |
|---|---|---|---|---|
| 4,966,131 A | * | 10/1990 | Houghton ............. | B06B 1/0253 601/2 |
| 5,551,416 A | * | 9/1996 | Stimpson .......... | A61M 15/0085 128/200.14 |
| 7,309,948 B2 | * | 12/2007 | Kuniyasu ............... | B06B 1/0629 600/459 |
| 2003/0015977 A1 | * | 1/2003 | Lee ....................... | B06B 1/0261 318/114 |
| 2003/0028341 A1 | * | 2/2003 | Fallon ................... | G01S 7/5205 702/117 |

(Continued)

*Primary Examiner* — Michael Rozanski (57) ABSTRACT

Sub-performing elements of an ultrasound transducer array are detected. The power, such as current, used by or provided to the transmit driver is measured. By driving each element or group of elements separately, defective elements or groups of elements are detected from the amount of power used.

20 Claims, 2 Drawing Sheets

(56) References Cited

U.S. PATENT DOCUMENTS

| | | |
|---|---|---|
| 2004/0236223 A1 | 11/2004 | Barnes et al. |
| 2004/0258127 A1 | 12/2004 | Ramamurthy et al. |
| 2005/0148873 A1 | 7/2005 | Petersen et al. |
| 2005/0171431 A1 | 8/2005 | Petersen |
| 2011/0080138 A1* | 4/2011 | Nakanishi ............ H02J 7/0016 320/116 |
| 2012/0267981 A1 | 10/2012 | Morris et al. |
| 2013/0296743 A1 | 11/2013 | Lee et al. |
| 2014/0005521 A1* | 1/2014 | Kohler ................ A61B 8/0841 600/411 |
| 2014/0184383 A1* | 7/2014 | Wodnicki ............. G08C 19/00 340/4.3 |
| 2015/0146502 A1* | 5/2015 | Kato .................... B06B 1/0292 367/137 |

\* cited by examiner

FIG. 1

ADC reading   FIG. 2

FIG. 3

SUB-PERFORMING TRANSDUCER ELEMENT DETECTION FOR MEDICAL ULTRASOUND

RELATED APPLICATIONS

The present patent document claims the benefit of the filing date under 35 U.S.C. § 119(e) of Provisional U.S. Patent Application Ser. No. 61/913,182, filed Dec. 6, 2013, which is hereby incorporated by reference.

BACKGROUND

The present embodiments relate to ultrasound transducers. In particular, whether the transducer performs properly is determined.

Ultrasound diagnostic imaging and therapy use arrays of transducer elements. During manufacture, one or more elements may be defective, such as due to shorting, inoperable driver, faulty connection, delamination of element layers, or other defect. Due to use, one or more elements may become defective, such as due to dropping, wear, or other damage.

For a one dimensional array, such as of 64-128 elements, one or more inoperable or otherwise poor performing elements may result in undesired imaging artifacts. As a result, any defective elements are undesired. In larger arrays, such as those becoming more common with two-dimensional (2D) arrays, some elements may typically be defective, either initially due to manufacturing defects or after some time due to degradation or damage. Usually, it is acceptable if some amounts of these elements are non-functional, especially if the defective elements are sparsely populated. If several elements in one area are defective, the overall array may not be acceptable due to side lobes or loss of sensitivity when certain apertures are selected.

To test for defective elements, special test equipment is used. For example, a transducer may be positioned in a liquid-filled tank and the acoustic output of each element is measured with a hydrophone. This time consuming and cumbersome external testing may be sufficient during manufacturing, but not optimal, for one-dimensional arrays. For 2D arrays or for measurements of any array in the medical environment, this approach may not be possible or desired. Given thousands of elements of a 2D array, testing may be slow even if attempted during manufacture.

BRIEF SUMMARY

By way of introduction, the preferred embodiments described below include methods, transducer probes, and systems for detecting sub-performing elements. The power, such as current, used by or provided to the transmit driver is measured. By driving each element or group of elements separately, defective elements or groups of elements are detected from the amount of power used.

In a first aspect, an ultrasound system is provided. A transmit driver is connectable or connected with ultrasound transducer elements of an array. A power source connects with the transmit driver. A current sensor is positioned to sense current from the power source provided to the transmit driver. A processor is configured to detect a defective element of the ultrasound transducer elements based on the current.

In a second aspect, a method is provided for detecting a sub-performing element. A power consumed by generating a transmit waveform for a transducer element of an array is sensed. An operational state of the transducer element is determined as a function of the power. The operational state is one of sub-performing and performing.

In a third aspect, an ultrasound system is provided. A transducer includes a multi-dimensional array of elements. First and second transmitter chips connect with first and second groups of the elements, respectively. First and second sensors are configured to sense a characteristic of power supplied to the first and second transmitter chips, respectively. A processor is configured to determine performance of the elements from the characteristics sensed by the first and second sensors.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Instead of using external test equipment (e.g., hydrophone), the power used by the transmit driver may be measured to detect sub-performing elements. This power-based measurement allows integration of the sensing and testing within the ultrasound system, providing for field testing and/or testing during manufacture. Since 2D arrays typically include many transmit driver chips in a modular approach, sensing may be performed modularly (e.g., sense power for each chip in parallel), reducing the time for detecting sub-performing elements in an array with hundreds or thousands of elements.

Figure 1:
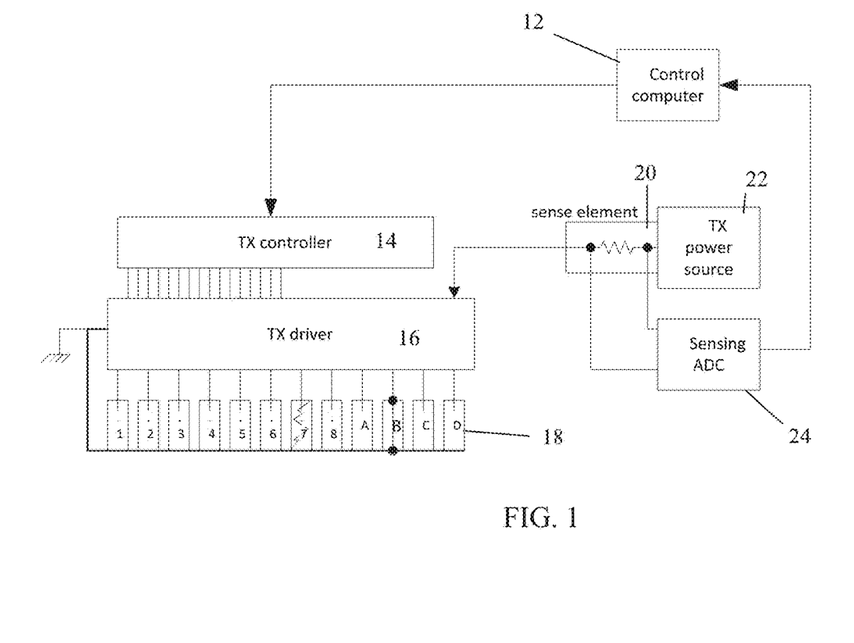
FIG. 1 is a block diagram of one embodiment of an ultrasound system for detecting sub-performing elements.

FIG. 1 shows an ultrasound system. The ultrasound system may be integrated within a diagnostic or therapeutic ultrasound system, such as being part of or within a housing of a handheld, cart-mounted, or other system for scanning or treating patients. For example, the ultrasound system is included in the components shipped to end-users for use with patients. The transmit driver 16, power source 22, current sensor (sense element 20 and analog-to-digital converter 24), and processor (e.g., control computer 12) are in an ultrasound imaging or therapy system, such as being within a same housing or housings as other components. Part of the system may be in a separate transducer, or the system, other than the array, is in a main system housing for testing elements of any connected array. This integrated system may be used to test for sub-performing elements during manufacture, after manufacture but before shipping, or in the field after shipping.

Alternatively, the ultrasound system includes one or more non-integrated components, such as the control computer 12, sense element 20, and/or sensing analog-to-digital converter 24. One or more components are part of a test rig or arrangement separate from the diagnostic imaging or therapeutic ultrasound system.

The ultrasound system includes a control computer 12, a transmit controller 14, a transmit driver 16, an array 18 of elements (e.g., 1-8 and A-D), a sense element 20 and analog-to-digital converter 24 of a sensor, and a transmit power source 22. Additional, different, or fewer components may be provided. For example, detectors, filters, scan converters, user input, and/or a display are provided. As another example, the transmit controller 14 is combined with the transmit driver 16 into a beamformer. In yet another example, the control computer 12 is integrated with the transmit controller 14. The analog-to-digital converter 24 may be part of the transmit driver 16, the transmit controller 14, or the control computer 12 or is a separate component.

The array 18 includes a plurality of ultrasound transducer elements 1-8 and A-D. The elements 1-8 and A-D each include a layer of transducer material. The layer of transducer material is a solid piezoelectric ceramic, composite, or other transduction material. Alternatively, the layer is a semiconductor with microelectromechanical devices for transduction, such as a plurality of drums or membranes and associated electrodes (e.g., capacitive membrane ultrasound transducer (CMUT)). The elements 1-8 and A-D may include electrodes, backing, and/or matching layers. A grounding plane may be included above or below any matching layers for grounding the top side of the elements 1-8 and A-D. The elements 1-8 and A-D may be multi-layer elements, such as two or three layers of piezoelectric with corresponding electrodes.

The transducer material is diced or formed into the plurality of elements 1-8 and A-D. Sub-elements may also be formed. The elements and corresponding kerfs align with the element contacts for separate electrical operation. In other embodiments, the elements 1-8 and A-D are formed by etching or other semiconductor processes.

The elements 1-8 and A-D are spaced in a two, 1.25D, 1.5D, 1.75D, or other multi-dimensional array of elements. For a multi-dimensional array of elements (matrix array), the elements 1-8 and A-D are spaced in a rectangular grid in elevation and azimuth. Each element is a cube or other volume shape. The elements are distributed over different dimensions, such as being distributed in an N×M grid where both N and M are greater than one. Other grids may be used, such as hexagonal or triangular. The multi-dimensional array may include hundreds or thousands of elements (e.g., 18,000 elements). Alternatively, the elements are spaced in a one dimensional pattern, such as being a single row of 64-128 elements along a line or curve.

Each element includes electrodes on opposite faces or parts of the element. One electrode connects with or is connectable through switches with the transmit driver 16. This electrode is a signal electrode for transmit operation and/or for receiving electrical waveforms or pulses. The signal electrodes of different elements are electrically isolated from each other. The other electrode is a ground electrode. The ground electrode may be on the side of the element where acoustic signals are transmitted and received from the patient (e.g., the face of the transducer). The electrodes are deposited on the elements 1-8 and A-D, formed by conductors on flex material (e.g., grounding plane on the side of the element for transmitting and receiving), or formed by wires, conductive surfaces, or other conductor.

In one embodiment, the array 18 is an ultrasound therapy array. The arrangement of the elements, size of the array, cooling components, and/or other characteristic of the array 18 are configured for applying high amplitude ultrasound lasting for many cycles. Alternatively or additionally, the array 18 is an ultrasound diagnostic imaging array. The characteristics of the array 18 are configured for scanning a patient for imaging with relatively lower amplitudes and/or pulse durations.

The transmit driver 16 connects with the elements 1-8 and A-D of the array 18. Separate electrical connections or channels (e.g., transmit beamformer channels) connect to separate elements 1-8 and A-D. The transmit driver 16 connects with the elements 1-8 and A-D of the array 18 for transmit and/or receive operation. Conductors electrically connect the transmit driver 16 to the array 18. The conductors are traces on flexible circuit material, solder bumps connected to electrodes or pads, wire bonds, or other conductor. The conductors may include portions for exposure on a surface for contact with electrodes of elements 1-8 and A-D and portions for contacting input/output pads of the transmit driver 16.

The connection is fixed, such as providing the connection with solder bumps or direct connect. In other embodiments, the transmit driver 16 is connectable with the array 18. One or more switches, such as in a multiplexer separate from or integrated with the transmit driver 16, may electrically connect different channels to different elements 1-8 and A-D. A physical connection, direct or indirect, within a housing or between housings with a cable, is provided, but the electrical connection may be disconnected.

The transmit driver 16 is a semiconductor chip, analog components, digital components, processors, field programmable gate arrays, memories, combinations thereof, circuit, or other components. In one embodiment, the transmit driver 16 is an integrated circuit, such as application specific integrated circuit (ASIC) manufactured as a chip.

The transmit driver 16 includes transistors or other switches for generating an electrical transmit waveform. One or more transistors for creating alternating pulses, such as a uni-polar or bi-polar pulse sequence, are provided for each channel or element 1-8 and A-D. In one embodiment, the ASIC includes pulsers. The transmit driver 16, with or without the transmit controller 14, may be a transmit beamformer, such as including delays, phase rotators, amplifiers, summers, or other components for relatively delaying and apodizing transmit apertures. The transmit driver 16 includes the entire or any portion of the beamformer, such as a clock, control, and signal routing.

A single chip or circuit with pulsers or other waveform generators of the transmit driver 16 may connect or be connectable with all of the elements 1-8 and A-D. In other embodiments, more than one transmit driver 16 is used. For example, two or more (e.g., 8, 16, 32, or 64) transmit drivers 16 and corresponding circuits and/or chips are provided. A modular approach is used for driving the array 18. Different groups of elements 1-8 and A-D connect or are connectable with different transmit drivers 16. For example, eight transmit drivers 16 are provided where each of the eight transmit drivers 16 connects with different groups of 36 elements 1-8 and A-D each.

The transmit drivers 16 of each chip and/or circuit are of the same type. The same design is used in a modular fashion. For example, a given application specific integrated circuit and corresponding semiconductor chip is the same as another application specific integrated circuit and corresponding semiconductor chip. Two parts are provided, but the two parts are of the same design. More than one type may be used, such as one type of transit driver 16 for one group of elements 1-8 and A-D and another type of transmit driver 16 for another group of elements 1-8 and A-D.

The power source 22 is a voltage or current source. For example, the power source 22 is a transformer connected with a power supply or mains power for converting alternating current to direct current. The current source provides current for driving by the transmit driver 16. The transmit driver 16 draws power from the power source 22 to generate electrical transmit waveforms, causing the elements 1-8 and A-D to create acoustic wave fronts.

The power source 22 connects with the transmit driver 16. The connection may be direct, such as through a wire or trace on a circuit board, or may be indirect, such as through one or more switches and/or the sense element 20. In one embodiment, each transmit driver 16 is on a chip and includes a pad or conductor for connection with a power rail supplied by the power source 22 with an intervening sense element 20. The sense element 20 connects with the power delivery system providing the transmit energy to the array 18.

The sense element 20 and the analog-to-digital converter 24 form a power sensor. In the embodiment shown in FIG. 1, the power sensor is a current sensor. The analog-to-digital converter 24 connects across a resistor as the sense element 20. The voltage drop across the known resistance indicates the current supplied to the transmit driver 16 by the power source 22. The analog-to-digital converter 24 digitizes samples representing the current through the sense element 20. The converter 24 quantifies the transmit power.

The sense element 20 and/or analog-to-digital converter 24 are within the transmit driver 16, such as in the ASIC, connect to the power input of the ASIC, are on a circuit board hosting or supporting the transmit driver 16 and/or the power rail, or otherwise are in the connection of the power source 22 to the transmit driver 16.

Other current sensors may be used. Voltage sensors may be used instead. Any sensor of a characteristic of the power drawn by or used by the transmit driver 16 may be used. In one embodiment, an amplifier is provided to amplify the voltage difference across the sense element 20. In the embodiment, a filter is provided to filter the output of the amplifier. The filter has a 1 ms or other time constant. In other embodiments, amplification and/or filtering is not provided.

The sensor quantifies the transmit power used by the transmit driver 16. Due to parasitic capacitance and other interference, driving one element 1-8 and A-D may be affected by other elements 1-8 and A-D also connected to the same transmit driver 16. A separate sequential measure of the power used to drive each element 1-8 and A-D connected with the transmit driver 16 may be performed. Due to interference or parasitic capacitance within the transmit driver 16 and/or between elements 1-8 and A-D, the sensitivity may vary. More elements 1-8 and A-D connected to the transmit driver 16 result in less sensitivity. The resolution of the analog-to-digital converter 24 is higher (greater number of bits) to deal with less sensitivity. A trade-off is provided between converter 24 resolution and number of elements 1-8 and A-D per transmit driver 16.

Where multiple transmit drivers 16 are provided, separate sensors may be provided. A sensor is connected, connectable with, or integrated with each transmit driver 16. For each transmit driver 16, the power to drive each element 1-8 and A-D is measured by the sensor sequentially. Using separate sensors (e.g., sense element 20 and converter 24 unique to each transmit driver 16), each transmit driver 16 may operate simultaneously to measure for different elements 1-8 and A-D. For example, two transmit drivers 16 and corresponding separate sensors connect with two groups of 36 elements 1-8 and A-D. The power to drive one element connected with one transmit driver 16 is measured at the same time as measuring the power to drive a different element connected to the different transmit driver 16. In the time to cycle through measuring each of the 36 elements, 72 elements are measured due to the parallel operation. In alternative embodiments, the same sensor connects with different chips or transmit drivers 16. Different sensing elements 20 may connect with different transmit drivers 16, but the same converter 24 may be used to measure the power, such as time multiplexing the converter 24.

The transmit controller 14 is a beamformer controller or other controller of the transmit driver 16. For example, the transmit controller 14 includes transistors and/or a circuit for selecting different pulsers of the transmit driver 16 and causing the pulsers to generate waveforms of a given length or duration. Delays, clocking, or other components for relative delays or phasing of the waveform generators of the transmit driver 16 may be provided in the transmit controller 14.

For detecting element performance, the transmit controller 14 is configured by software, loaded control information, hardware, or design to cause the transmit driver 16 to drive individual ones or particular groups of the elements 1-8 and A-D at a given time. The transmit controller 14 provides controls for aperture control in driving during therapy and/or imaging. The same controls may be used to select a small or single element aperture and to drive the selected aperture.

During detection of performance, the transmit controller 14 causes driving of imaging or therapy waveforms. Alternatively, waveforms designed for performance sensing are used, such as generating a pulse train of 10-50 cycles with a uniform envelope. Any pulse train or waveform may be generated for sensing, such as any number of cycles with any envelope. In one embodiment, transmit waveforms used for continuous wave Doppler with hundreds of cycles are used to allow the analog-to-digital converter 24 to settle during a measurement. In another embodiment, thousands of cycles may be used.

In one embodiment, the transmit controller 14 is a separate chip and/or circuit than the transmit driver 16, such as the transmit driver 16 including high voltage switches or pulsers, and the transmit controller 14 including low voltage switches or control for operating the pulsers. In other embodiments, the transmit controller 14 or parts of the transmit controller 14 are included in a same chip, ASIC, or circuit as the transmit driver 16.

The control computer 12 is a processor, controller, or other circuit for detecting performance of the elements 1-8 and A-D from the sensed power consumption and/or for causing the transmit controller 14 to perform the sequence of transmissions for measuring. In one embodiment, the control computer 12 is a processor of a therapy or imaging system. In another embodiment, separate components provide the separate functions of detecting and controlling.

The control computer 12 is a processor, such as a control processor, general processor, digital signal processor, graphics processing unit, application specific integrated circuit, field programmable gate array, network, server, group of processors, data path, combinations thereof or other now known or later developed device for determining whether an element is performing properly or not. The processor 18 is configured by software and/or hardware to perform the acts.

The control computer 12 is configured to check each or groups of the ultrasound transducer elements 1-8 and A-D.

The transmit controller 14 is instructed to select the elements 1-8 and A-D or groups of elements 1-8 and A-D sequentially per transmit driver 16 and cause the transmit driver 16 to drive the selected elements 1-8 and A-D. In response, the transmit driver 16 drives the selected elements 1-8 and A-D. The control computer 12 causes the analog-to-digital converter 24 to measure the current or other characteristic of power drawn by or used by the transmit driver 16 for each or group of elements 1-8 and A-D.

Figure 2:
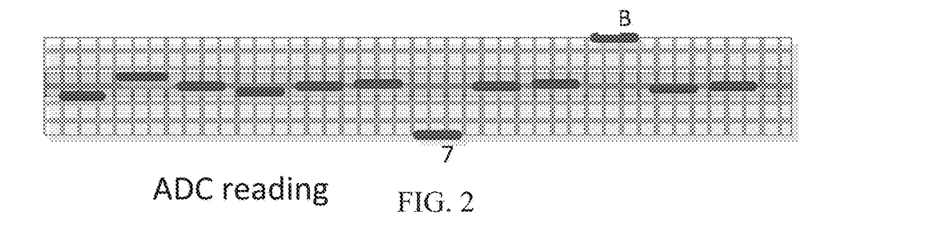
FIG. 2 illustrates example current measurements for the array of FIG. 1.

FIG. 2 shows an example. Each bold line represents a power measurement for one of the elements 1-8 and A-D of the array 18 of FIG. 1. Driving some elements with a same waveform draws the same amount of power, such as elements 3, 5, 8 and D. Other elements draw different power for being driven with the same waveform (e.g., compare elements 1 and 2). Element 7 is shown drawing relatively little or no power, such as associated with a defect resulting in no operation of the pulser and/or open circuit operation of the element. Element B is shown as drawing a comparatively lot of power, such as associated with a short circuit in the element B or the circuit driving element B. The power may be an average, maximum, mean, median, or other measure during operation. The power used may instead be a sample measured at a particular time relative to the start of driving the element 1-8 and A-D.

Using the sensed power characteristic (e.g., sensed current magnitude), the control computer 12 detects whether one of the elements 1-8 and A-D is defective. A defective element 1-8 and A-D may be performing or operating, but in a way that is undesired. Any threshold may be used to distinguish satisfactory performance from sub-performance. For example, a current, average current, other current outside a range of expected or sufficient operation shows sub-performing. The range of expected operation may be predetermined, empirically determined for transducers in general, empirically determined for a type of transducer, determined based measures of other elements 1-8 and A-D of the same array, determined based on theory, determined based on tolerances, or determined based on other information. Using statistics (e.g., measures from known-good arrays), the normalized value or range of power is used to compare with the power sensed for each section or element 1-8 and A-D.

The power draw for the element 1-8 and A-D (e.g., elements 7 and B in the example of FIG. 2) may fall outside the range by drawing more power or less power. Either case indicates a sub-performing element 1-8 and A-D. The control computer 12 examines the sensed power to drive the elements 1-8 and A-D and detects any defective elements 1-8 and A-D based on the power, such as based on sensed current. A defective element 1-8 and A-D will have significantly less power use if open or defective or will have substantially more power use if shorted. The control computer 12 examines the sensed power characteristic (e.g., integral of current, average current, or other) to determine the performance of an element 1-8 and A-D.

By examining the currents for driving the different elements 1-8 and A-D or groups of elements 1-8 and A-D, the control computer 12 detects any defective elements 1-8 and A-D or groups. The decision for each element 1-8 and A-D may be binary, such as within the range (satisfactorily performing) or outside of the range (sub-performing). Alternatively, different ranges may be used or an amount of difference from thresholds used to measure a significance of the sub-performance and/or satisfactory performance. In the example of FIG. 2, element 1 is at the edge of the satisfactory range, so may be noted as performing, but in a less satisfactory way than element 3, for example.

In one embodiment, identifying one element 1-8 and A-D as sub-performing is indicated to the manufacturer, user, technician, or other by the control computer 12. A message is transmitted and/or displayed. In other embodiments, more than one element 1-8 and A-D is identified before sending a message. In a 2D array, the control computer 12 may indicate an array 18 as defective when tens or hundreds of elements are sub-performing. The identification may be weighted by the magnitude of the lack of performance (e.g., difference from the range of satisfactory) and/or a measure of distribution of the sub-performing elements 1-8 and A-D (e.g., measure of sparseness).

In a modular approach, the control computer 12 may rapidly test all of the elements 1-8 and A-D of an array of many elements 1-8 and A-D, such as thousands. By testing multiple elements 1-8 and A-D at a time where each simultaneously tested element 1-8 and A-D is connected with a unique or different chip or circuit, the testing may be more rapid than sequencing through each element 1-8 and A-D, separately. For example, 8 ACISs connect with 288 elements (e.g., each ASIC connects with 36 elements 1-8 and A-D). 8 elements 1-8 and A-D may be tested at one time by sensing the ASIC driving current for each of the 8 single elements 1-8 and A-D driven by the 8 ASICs. This is repeated 35 times to determine performance level for all the 288 elements 1-8 and A-D. Any number of elements 1-8 and A-D of each group of 36 may be determined as defective.

In one embodiment, the ultrasound system uses the modular approach for detecting sub-performing elements 1-8 and A-D. A transducer with a multi-dimensional array 18 of elements 1-8 and A-D includes at least two transmitter chips connected with different groups of the elements 1-8 and A-D. The transmitter chips and array 18 are configured for therapeutic ultrasound. A therapy transducer is provided. To test for defective elements 1-8 and A-D, separate sensors connect with each of the transmitter chips. The connection is configured so that a characteristic of power supplied to the transmitter chips is sensed. All or part of the sensors may be integrated into or be part of the transmitter chips. A processor is configured to determine performance of the elements from the characteristics sensed by the multiple sensors.

The sensors are integrated within a medical ultrasound system used for patients, so the determination of performance of the elements may be performed periodically, as desired, or at other times. Rather than relying on a test structure at manufacture, the determination may be made by the system used for patients itself. Feedback may be provided to the physician or technician about the quality of the array at the point or location of use, aiding in decisions whether to replace the array and/or indicating when an array should be replaced.

One or more memories may be provided for the transmit controller 14 and/or the control computer 12. The memory is a non-transitory computer readable storage medium having stored therein data representing instructions executable by a programmed processor. The instructions, by being loaded into or available to the processor, configure the processor(s). The processor operates pursuant to instructions stored in the memory. The instructions for implementing the processes, methods and/or techniques discussed herein are provided on the computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 3:
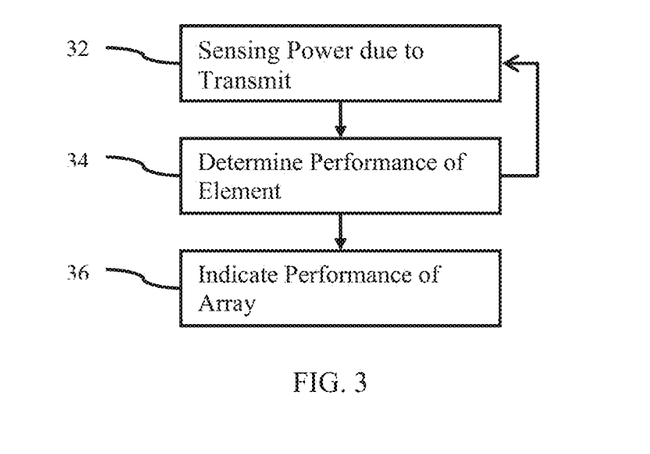
FIG. 3 is a flow chart diagram of one embodiment of a method for detecting sub-performing elements.

FIG. 3 shows one embodiment of a method for detecting a sub-performing element. Different elements are tested in order to identify any that may be sub-performing. The testing is for elements of a multi-dimensional transducer array, but may be for elements of a one-dimensional array.

The method is performed in the order shown. Alternatively, a different order is provided. Additional, different, or fewer acts may be provided. For example, acts for configuring a transmitter for selecting and/or driving individual elements are provided. As another example, an act for preventing operation with an array having a large number of sub-performing elements is provided.

The acts are performed using the system of FIG. 1 or a different system. For example, a current, voltage, or other power sensor performs act 32. A processor performs act 34. The processor, using a display, speaker, printer, memory, or transmission on a network performs act 36. Other devices may perform any of the acts.

The method is performed without placing the transducer against the patient. For example, the transducer is placed against a phantom, bed, or other material. Alternatively, the transducer is placed against a person but with mitigation of unintended or non-controlled energy input into the body. For example, the elements are fired 180 degrees out of phase, which make peak lobes off to the sides, or using random phases, with the intent to de-focus the energy as much as possible. In a large therapy array, one element from each area (e.g., one element from each module) is used to transmit a few thousand cycles so the energy input to the patient is low and spread out.

In act 32, the power consumed by generating a transmit waveform for a transducer element of an array is sensed. The current, voltage, or other characteristic of power is sensed. The power drawn by or used by the pulser, waveform generator, or other transmit driver to cause the element to transduce to acoustic energy is sensed.

The sensing occurs during a testing process. Aperture control or other process causes activation or driving of one element per transmitter or per transmitter chip. This allows the power drawn by a single element connected with the transmit chip to be measured. Alternatively, the aperture control is used to drive more than one of the elements, such as associated with testing groups of elements for performance. The power may be sensed during imaging or therapy use rather than during a testing specific procedure in other embodiments. Depending on the apertures being used, the performance of the array or group of elements may be tested during regular use. Detecting that one or few elements are sub-performing when the aperture includes many elements may require higher resolution sensing. Any sub-performance by an element may be identified without identifying the specific element.

Where the transmitter includes modules or repetition of separate circuits for driving different elements, the sensing may be performed separately for each. The sensing for each module or separate circuit is performed in parallel. For element specific sensing, the sensing for each module or separate circuit sequences through driving and sensing the different connected elements. By performing this sequence in parallel for the different modules or separate circuits, a greater number of elements may be tested in a given time than if sequencing through all elements.

In one performance of act 32, the power to drive more than one element may be sensed at a given time. The sensing may be for a group of elements, and/or the sensing may be performed for each of multiple modules or separate circuits.

In act 34, an operation state of the transducer element or elements sensed in act 32 is determined. The operation state may be binary, such as performing and sub-performing options. If the sensed power is outside a range of acceptable powers, the element is sub-performing. If the sensed power is within the range of acceptable powers, the element is performing. The range is determined empirically or by theory. The range may be for elements in general, for a type of element, for a type of array, for a specific array, and/or for specific elements. The range represents power drawn to drive an element that is not shorted or open circuited and/or that operates to provide sufficient imaging and/or therapy. In alternative embodiments, a non-binary operation state is determined. For example, the level of performance and/or sub-performance is determined. Other threshold ranges and/or measures of magnitude may be used to indicate the non-binary level of performance.

The determination uses the power sensed in act 32. The power may be a current, voltage, or combination thereof. Other characteristics of power used for driving may be used. Since the driving waveform for sensing may be multiple cycles, the sensed power may include multiple measures over time. An average, integral, sum, or other statistical combination of the measures of the power may be calculated. From this calculated value or values, the operation state is determined.

Where the sensing for a given iteration is of multiple elements (i.e., one measure during driving by the same transmitter or chip of multiple elements), the determination is for the multiple elements. The multiple elements are performing or sub-performing. In the modular approach using separate sensors, the operation state of each element or group of elements associated with each sensor is determined. Where a given sensor senses the power to drive multiple elements at a same time, the operation state of the group of elements is determined. The thresholds may be set to identify that one or more of the group of elements is sub-performing.

Acts 32 and 34 may be repeated. The sensing and determination are repeated so that the operation state of each of all or some of the transducer elements of an array is determined. In one embodiment, the repetition occurs sequentially through all of the elements or groups of elements. In another embodiment, the repetition occurs at a same time for each of a plurality of modules. The repetition may continue until one or other number of sub-performing elements is identified and/or until all of the desired elements are tested.

In an alternative embodiment, the acts 32 and 34 are not repeated. Instead, one or more elements thought to be defective or for which testing is desired are tested without testing other elements.

In act 36, an indication of the operation of the array and/or one or more transducer elements is output. The output is to a display, such as displaying the measures of all the elements in a table or graph (e.g., see FIG. 2). Alternatively, the output is to a printer, memory, or by transmission.

The indication is of operation of the array in one embodiment. If no or only a low number of transducer elements are sub-performing, the indication may be that an array may be used and/or sold. If one or above the number of transducer elements are sub-performing, the indication may be that the array is not to be used, should be discarded, should be fixed, or may be used with a warning of undesired operation. The number is a threshold specific to the type of array of transducer elements, set by the user, set by the manufacturer, and/or established in another manner. Once a sufficient number of elements, with or without consideration of sparse distribution and/or magnitude of defect, are determined to be defective, the indication is provided that the array is not operational or operates with sub-standard performance. In the case of an array of thousands of elements, the number may be higher than for an array with tens or hundreds of elements.

In other embodiments, the indication is of operation of specific transducer elements. Instead of or in addition to indication of operation of the array, the operation of transducer elements is indicated. A number of sub-performing elements, identities of the sub-performing elements, a map of the sub-performing elements, an indication of a likely result of the sub-performing elements, the magnitude of the defects, the type of possible defects, or other information may be output to a user, technician, and/or manufacturer.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound system comprising:
    an array of ultrasound transducer elements;
    a transmit driver connectable or connected with the ultrasound transducer elements of the array;
    a power source connected with the transmit driver;
    a current sensor connected between the power source and the transmit driver to sense current from the power source provided to the transmit driver; and
    a processor configured to detect a defective element of the ultrasound transducer elements based on the current.

2. The ultrasound system of claim 1 wherein the array comprises a multi-dimensional array of thousands of the ultrasound transducer elements.

3. The ultrasound system of claim 1 wherein the transmit driver comprises an application specific integrated circuit including pulsers for applying alternating pulses to the elements.

4. The ultrasound system of claim 1 wherein the transmit driver comprises a plurality of channels connectable with respective ones of the ultrasound transducer elements.

5. The ultrasound system of claim 1 wherein the current sensor comprises a resistor and an analog-to-digital converter connected across the resistor.

6. The ultrasound system of claim 1 wherein the power source comprises a direct current source.

7. The ultrasound system of claim 1 wherein the processor is configured to detect the defective element where the current is outside a range of operation for the array.

8. The ultrasound system of claim 1 further comprising a transmit controller, the transmit controller configured to cause the transmit driver to drive individual ones of the ultrasound transducer elements in sequence;
    wherein the current sensor is configured to sense the current to the transmit driver for each of the ultrasound transducer elements during the driving; and
    wherein the processor is configured to check each of the ultrasound transducer elements based on the sensed currents.

9. The ultrasound system of claim 1 wherein the transmit driver is in a first chip connected to a first sub-set of the ultrasound transducer elements;
    further comprising:
    another transmit driver of a second chip connected to a second sub-set of the ultrasound transducer elements;
    another current sensor positioned to sense another current from the power source provided to the second chip;
    wherein the processor is configured to detect the defective element of the first sub-set based on the current and is configured to detect another defective element of the second sub-set based on the other current.

10. The ultrasound system of claim 1 wherein the array comprises an ultrasound therapy array.

11. The ultrasound system of claim 1 wherein the transmit driver, power source, current sensor, and processor are in an ultrasound imaging system.

12. A method for detecting a sub-performing element, the method comprising:
    sensing a power drawn by a transmit driver generating an electrical transmit waveform output to a transducer element of an array; and
    determining an operational state of the transducer element as a function of the power, the operational state being one of sub-performing and performing.

13. The method of claim 12 wherein sensing the power comprises sensing a current draw by the transmit driver.

14. The method of claim 12 wherein determining comprises determining that the operational state is sub-performing where the power is outside a range of powers.

15. The method of claim 12 further comprising repeating the sensing and determining for each of a plurality of transducer elements of the array.

16. The method of claim 12 wherein different transmit driver chips connect with different groups of transducer elements of the array, and wherein sensing and determining is performed separately for each one of the groups.

17. The method of claim 12 further comprising indicating whether the array is sub-performing or not as a function of a number of elements of the array determined to be sub-performing.

18. An ultrasound system comprising:
    a transducer comprising a multi-dimensional array of elements;
    first and second transmitter chips connected with first and second groups of the elements, respectively;
    first and second sensors between a power supply and the first and second transmitter chips to sense a characteristic of power supplied from the power supply to the first and second transmitter chips, respectively; and a processor configured to determine performance of the elements from the characteristics sensed by the first and second sensors.

19. The ultrasound system of claim 18 wherein the transducer comprises a therapy transducer.

20. The ultrasound system of claim 18 wherein the first and second sensors are integrated within a medical ultrasound system used for patients.

* * * * *